(12) United States Patent
Pagoria et al.

(10) Patent No.: US 9,458,115 B2
(45) Date of Patent: Oct. 4, 2016

(54) SYNTHESIS OF SUBSTITUTED PYRAZINES

(75) Inventors: Philip F. Pagoria, Livermore, CA (US); Mao Xi Zhang, Mountain House, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 1742 days.

(21) Appl. No.: 12/426,774

(22) Filed: Apr. 20, 2009

(65) Prior Publication Data

US 2010/0267955 A1    Oct. 21, 2010

(51) Int. Cl.
   *C07D 241/20* (2006.01)
(52) U.S. Cl.
   CPC .................... *C07D 241/20* (2013.01)
(58) Field of Classification Search
   CPC ..................................... C07D 241/20
   USPC ....................................... 544/336
   See application file for complete search history.

(56) References Cited

U.S. PATENT DOCUMENTS 4,560,756 A    12/1985    Brunnmueller et al.

FOREIGN PATENT DOCUMENTS

WO    2007/103832 A2    9/2007    ............. F02B 15/00

OTHER PUBLICATIONS

Dörwald, F. Zaragoza. Side Reactions in Organic Synthesis: A Guide to Successful Synthesis Design, Weinheim: Wiley-VCH Verlag GmbH & Co. KGaA, 2005, Preface.*
Pagoria et al., Synthesis, Scale-up and Experimental Testing og LLM-105 (2, 6-Diamino-3,5-dinitropyrazine-1-oxide) Insensitive Munitions and Energetic Materials Technology Symposium, Meeting No. 956; National Defence Industrial Association: San Diego, CA 1998.
Barot et al., "Heterocyclic Imines and Amines. Part XVI. 2,6 Diaminopyrazine and its 1-Oxide from Iminodiacetonitrile" J.A.J. Chem. Soc. Perkin Trans. Jan. 1973, 606-12.
Wolf et al., "tert-Butyl Hypochlorite: $(CH_3)_3COH+Cl_2+NaOH\rightarrow(CH_3)_3 COCl+NaCl+H_2O$" Org. Synth. Coll IV, 1963, p. 125.
Chang et al., "The unusually mild and facile basic hydrolysis of N-nitroso-2-(methylamino)acetonitrile" J. Org. Chem. 1976, 41, 3752-3755, DOI: 10.1021/jo00885a002, Publication Date (Web): May 1, 2002.
Chute et al., "Catalyzed Nitration of Amines: III. The Ease of Nitration Among Aliphatic Secondary Amines" Canadian, J. Chem. 1947, 114.
U.S. Appl. No. 12/130,444, filed May 30, 2008.
Li et al., "Theoretical Calculation and Molecular Design for High Explosives: Theoretical Study on Polynitropyrazines and Their N-oxides" Propellants, Explosives, Pyrotechnics 29 (2004). No. 4; p. 231-235.
Vohra et al., "New Synthesis of 2-Amino-6-alkoxypyrazines from N-Nitrosobis(cyanomethyl)amine and Alkoxides" 1979 American Chemical Society; Received Nov. 7, 1978.
He et al., "Molecular design of analogues of 2,6-diamino-3,5-dinitropyrazine-1-oxide" Journal of Molecular Structure (Theochem) 668 (2004) 201-208 www.elsevier.com/locate/theochem.
European Search Report from application No. 08166297.5-2122 mailed on Jan. 27, 2009.
Baughman, Ray H., "Muscles made from metal" Science, American Association for the Advancement of Science, US, Washington, DC, vol. 300, Apr. 11, 2003; pp. 268-269.
Kramer, D. et al., "Surface-Stress induced macroscopic bending of nanoporous gold cantilevers" Nano Letters American Chem. Soc. USA, vol. 4, No. 5, May 2004; pp. 793-796.
Weissmuller J. et al., "Charge-Induced reversible strain in a metal" Science, American Association for the Advancement of Science, US, Washington, DC, vol. 300, Apr. 11, 2003; pp. 312-315.
Bellamy, Anthony J. et al: "A new synthetic route to LLM-105 (2,6-diamino-3, 5-dinitropyrazine 1-oxide)". New Trends in Research of Energetic Materials, Proceedings of the Seminar, 11th, Pardubice, Czech Replublic, Apr. 9-11, 2008, vol. PT. 2, 466-475. Editor(s): Ottis, Jan; Pachman, Jiri. Publisher: University of Pardubice, Pardubice, Czech Rep. Code, 2008, XP008123857, p. 467.
Bellamy A. J. et al: The Study of Some Potential New Synthetic Routes to LLM-105 (2,6-Diamino-3,5-dinitropyrazine 1-oxide). Central European Journal of Energetic Materials, vol. 4, No. 3, 2007, pp. 33-57, XP008123860. ISSN: 1733-7178, pp. 39, 42.
International Search Report and Written Opinion from PCT Application No. PCT/US2010/031572 mailed Jul. 14, 2010.
Bellamy, Anthony J. et al., "A new synthetic rout to LLM-105 (2, 6-diamino-3, 5-dinitropyrazine 1-oxide)," New Trends in research of Energetic Materials, Proceedings of the Seminar, 11th, Pardubice, Czech Republic, Apr. 9-11, 2008, vol. Pt. 2, p. 466-475.

* cited by examiner

*Primary Examiner* — Douglas M Willis

(57) ABSTRACT

A method for synthesizing a pyrazine-containing material according to one embodiment includes contacting an iminodiacetonitrile derivative with a base and a reagent selected from a group consisting of hydroxylamine, a hydroxylamine salt, an aliphatic primary amine, a secondary amine, an aryl-substituted alkylamine a heteroaryl-substituted alkyl amine, an alcohol, an alkanolamine and an aryl alcoholamine. Additional methods and several reaction products are presented.

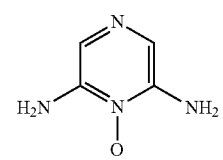

2,6-diaminopyrazine-1-oxide (DAPO)

33 Claims, 1 Drawing Sheet

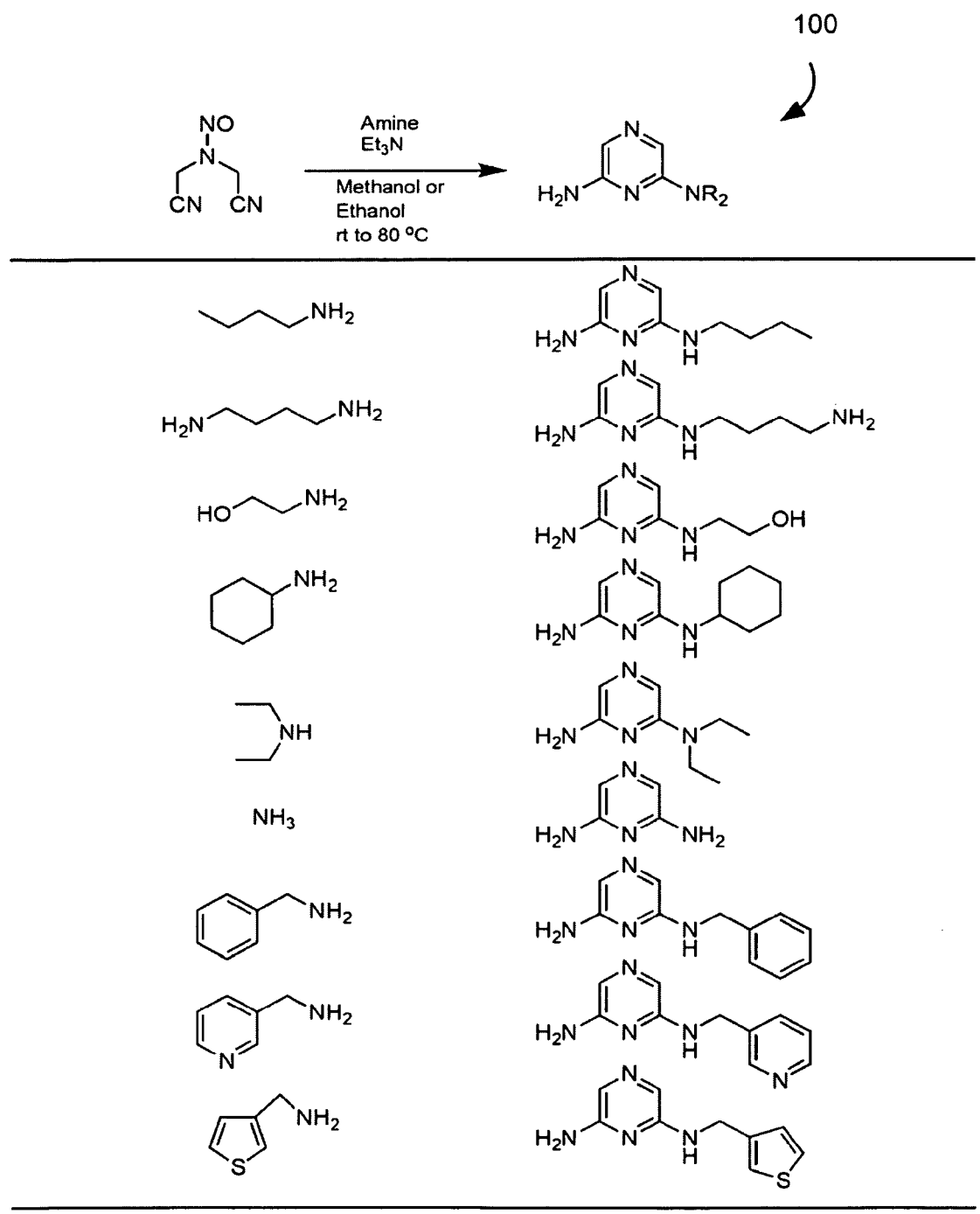

SYNTHESIS OF SUBSTITUTED PYRAZINES

The United States Government has rights in this invention pursuant to Contract No. DE-AC52-07NA27344 between the United States Department of Energy and Lawrence Livermore National Security, LLC for the operation of Lawrence Livermore National Laboratory.

FIELD OF THE INVENTION

The present invention relates to synthesis of organic compounds, and more particularly to synthesis of compounds such as 2,6-diaminopyrazine-1-oxide (DAPO) and 2,6-diamino-3,5-dinitropyrazine-1-oxide (LLM-105).

BACKGROUND 2,6-Diamino-3,5-dinitropyrazine-1 -oxide (LLM-105) was discovered at Lawrence Livermore National Laboratory in 1994. LLM-105 is a thermally stable, insensitive molecule with a crystal density of 1.918 g/cc and a decomposition point of >350° C. There have been several reported syntheses of LLM-105, most of them proceed through the intermediate compound, 2,6-diamino-3,5-dinitropyrazine (ANPZ), which upon oxidation with trifluoroacetic peracid yields LLM-105. The most attractive synthesis to date involves the nitration of 2,6-dimethoxypyrazine to 2,6-dimethoxy-3,5-dinitropyrazine followed by amination with ammonium hydroxide to yield ANPZ, and oxidation with trifluoroacetic acid and 50% $H_2O_2$. This gives LLM-105 in high yield that is contaminated with 3-10 % ANPZ. Over the years this synthesis has been refined and optimized to give LLM-105 in a 65% overall yield from 2,6-dichloropyrazine or 2,6-dimethoxypyrazine. The separation of ANPZ from LLM-105 in these mixtures has been very difficult and obtaining pure LLM-105 has been problematic.

The synthesis of DAPO was reported previously by the hydrogenation of 2-amino-6-hydroxaminopyrazine-1-oxide (AHAPO) in low total overall yield. The published procedure involved dissolving AHAPO in AcOH and treating it with $H_2$ at 45 psi at room temperature for 1 hour in the presence of Adam's catalyst ($PtO_2$). DAPO is a stable white solid with a melting point of 294-295° C.

The synthesis of LLM-105 by the nitration of DAPO was described previously in a patent application and later published by Bellamy and Golding in the Central European Journal of Energetic Materials in 2007.

What is therefore needed is a way to synthesize pyrazines such as DAPO in good yields and LLM-105 in a more efficient and inexpensive manner.

SUMMARY

A method for synthesizing a pyrazine-containing material according to one embodiment includes contacting an iminodiacetonitrile derivative with a base and a reagent selected from a group consisting of hydroxylamine, a hydroxylamine salt, an aliphatic primary amine, a secondary amine, an aryl-substituted alkylamine a heteroaryl-substituted alkyl amine, an alcohol, an alkanolamine and an aryl alcoholamine.

A method for synthesizing 2,6-diaminopyrazine according to one embodiment includes contacting an iminodiacetonitrile derivative with ammonia.

A method for synthesizing 2-amino-6-alkoxy(or aryloxy) pyrazine according to one embodiment includes contacting an iminodiacetonitrile derivative with a base and an alcohol.

A method for synthesizing 2,6-diaminopyrazine-1-oxide (DAPO) according to one embodiment includes contacting an iminodiacetonitrile derivative with a base and hydroxylamine or a hydroxylamine salt for forming DAPO.

A method for synthesizing 2-amino-6-(alkylamino)pyrazine according to one embodiment includes contacting an iminodiacetonitrile derivative with a base and an aliphatic or substituted aliphatic amine.

A method for synthesizing 2-amino-6-(arylalkylamino) pyrazine according to one embodiment includes contacting an iminodiacetonitrile derivative with a base and an aryl-substituted alkylamine.

A method for synthesizing 2,6-diamino-3,5-dinitropyrazine-1-oxide (LLM-105) according to one embodiment includes contacting 2,6-diaminopyrazine-1-oxide (DAPO) with nitric acid in the presence of sulfuric acid.

A method for synthesizing 2-amino-6-R-substituted-pyrazines according to one embodiment includes contacting N—X-bis(cyanomethyl)amine with a reactant selected from a group consisting of an alkylamine, an arylamine, an alkylalcohol, an arlyalkylalcohol, an etheralcohol, a tertiaryaminoalkylalcohol and an aryl alcohol in the presence of base for forming a 2-amino-6-alkylaminopyrazine, a 2-amino-6-arylaminopyrazine, a 2-amino-6-alkoxypyrazine, a 2-amino-6-arylalkylaminopyrazine, a 2-amino-6-etheralkoxypyrazine, a 2-amino-6-tertiaryaminoalkylalkoxypyrazine or a 2-amino-6-aryloxypyrazine, respectively.

Other aspects and embodiments of the present invention will become apparent from the following detailed description, which, when taken in conjunction with the drawings, illustrate by way of example the principles of the invention.

BRIEF DESCRIPTION OF THE DRAWINGS

FIG. 1 illustrates a general illustrative reaction for preparing aminopyrazines from N-nitroso-bis(cyanomethyl) amine according to one embodiment.

DETAILED DESCRIPTION

The following description is made for the purpose of illustrating the general principles of the present invention and is not meant to limit the inventive concepts claimed herein. Further, particular features described herein can be used in combination with other described features in each of the various possible combinations and permutations.

Unless otherwise specifically defined herein, all terms are to be given their broadest possible interpretation including meanings implied from the specification as well as meanings understood by those skilled in the art and/or as defined in dictionaries, treatises, etc.

It must also be noted that, as used in the specification and the appended claims, the singular forms "a," "an" and "the" include plural referents unless otherwise specified.

Some embodiments of the present invention include new methods of synthesis of 2,6-diaminopyrazine-1-oxide (DAPO), a precursor to 2,6-diamino-3,5-dinitropyrazine-1-oxide (LLM-105), an insensitive high-explosive. In one approach, DAPO is synthesized in good yields by allowing a hydroxylamine salt to react with an N-substituted iminodiacetonitrile followed by treatment with base. Other embodiments of the present invention include new general methodology for the synthesis of 2-amino-6-R-substituted-pyrazines by allowing an N-substituted iminodiacetonitrile to react with substituted amines or alcohols.

The inventors have surprisingly discovered that DAPO can be prepared directly from iminodiacetonitrile derivatives by allowing an iminodiacetonitrile derivative to react with hydroxylamine or a hydroxylamine salt in the presence of an appropriate base. Nitration of DAPO in various conditions produces LLM-105 in the yield of 30-80%.

In one general embodiment, a method for synthesizing a pyrazine-containing material includes allowing an iminodiacetonitrile derivative to react with a base and a reagent selected from a group consisting of hydroxylamine, a hydroxylamine salt (e.g. hydrochloride, sulfate, nitrate), an aliphatic primary amine, a secondary amine, an aryl-substituted alkylamine, a heteroaryl-substituted alkyl amine, an alcohol, an alkanolamine or an aryl alcoholamine.

General Conditions

Several approaches are presented below. In general, reactions may take place at a variety of temperatures, e.g., from about −15° C. to about 50° C, and in some approaches at about room temperature, e.g., about 20° C.±5° C. A typical synthesis involves dissolving N-Nitroso-bis(cyanomethyl) amine in Methanol at about 0-5° C., adding solid hydroxylamine hydrochloride (or sulfate) portion-wise at about 0-5° C., followed by the addition of triethylamine at less than about 15° C. The resulting clear yellow solution is allowed to stir at about 0-5° C. for about 0.5 hours, warming the mixture to about 20-25° C. and stirring for about 2 hours. DAPO forms as a precipitate that is collected by filtration and purified by recrystallization from a water/methanol mixture.

Precursor Synthesis

Synthesis of pyrazine-containing materials, such as those listed above, in some approaches starts with an iminodiacetonitrile derivative, such as an N—X-substituted iminodiacetonitrile, where X is a leaving group such as chloro (—Cl), nitroso (—NO), nitro (—NO$_2$), a hydroxyl or alkoxyl group (e.g. —OCH$_3$), ester [e.g. acetate (OAc), trifluoroacetate (OTFA), mesylate (—OMs), or tosylate (—OTs)], bromine (—Br), iodine (—I), or other leaving group known in the art.

The precursors, such as XN(CH$_2$CN)$_2$, are known compounds which can be prepared according to the literature. In one approach, iminodiacetonitrile (IDAN) [HN(CH$_2$CN)$_2$] may be converted to an N—X-substituted iminodiacetonitrile (1) according to the following reaction, where R=various functional groups such as —OH and X=NO, Cl or Br. However, other methods may also be used to create the iminodiacetonitrile derivative.

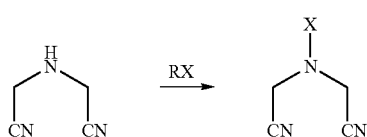

2,6-diaminopyrazine-1-oxide (DAPO) synthesis

As noted above, the inventors have surprisingly discovered that DAPO can be prepared directly from iminodiacetonitrile derivatives, such as XN(CH$_2$CN)$_2$ (where X=Cl, NO, NO$_2$, or other leaving group) by reacting the iminodiacetonitrile derivative with hydroxylamine or one or more hydroxylamine salts in the presence of an appropriate base (such as metal hydroxides (e.g., NaOH), metal carbonates (e.g., Na$_2$CO$_3$,), metal bicarbonates (e.g., NaHCO$_3$), pyridine, tertiary amines, secondary amines, metal alkoxides, and others). The yields of DAPO from the reactions are about 0-80%, depending on the reaction conditions and reagents.

One illustrative reaction is presented below.

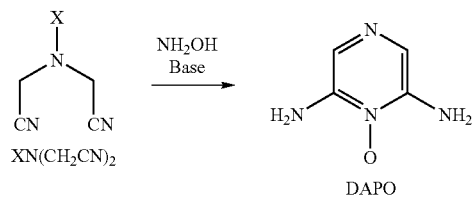

In one illustrative reaction, iminodiacetonitrile derivative, a hydroxylamine salt, and triethylamine are combined together in methanol at about 0-5° C. and allowed to warm to room temperature (e.g., about 20° C.±5° C.). The formed DAPO precipitates from the reaction mixture and may be collected by filtration. This illustrative approach has a DAPO yield of about 60-70%.

DAPO is a stable white solid with a melting point of about 294-295° C.

2,6-diamino-3,5-dinitropyrazine-1-oxide (LLM-105) synthesis from DAPO

A synthesis of LLM-105 based on the nitration of DAPO has several advantages over the procedure described above in the Background section, including reduced cost, improved safety and purer final product. The synthesis described herein does not produce an energetic compound until the final step, while in the syntheses that proceed through ANPZ energetic compounds are produced in each of the last three steps. There are added costs associated with the synthesis of energetic compounds, mostly due to additional safety requirements and fewer commercial companies authorized to produce energetic compounds. The syntheses that proceed through the ANPZ intermediate also results in a product that is contaminated (6-10%) with the starting material, 2,6-diamino-3,5-dinitropyrazine (ANPZ), resulting from the incomplete oxidation of ANPZ during the oxidation step. In the new synthesis presented herein according to one embodiment, the final nitration step starts with DAPO, which already possesses the N-oxide moiety, and essentially pure LLM-105 is produced. Finally, iminodiacetonitrile is an inexpensive, commercially available starting material. Thus the cost of synthesis of LLM-105 by the new method compared to the synthesis described above should be greatly reduced.

Nitration of DAPO in various conditions produces LLM-105 in the yield of about 0-95%.

In a general embodiment, DAPO is contacted with nitric acid in the presence of sulfuric acid for forming 2,6-diamino-3,5-dinitropyrazine-1-oxide (LLM-105). In one illustrative approach, the DAPO is treated with nitric acid (about 90-100% HNO$_3$) in the presence of fuming sulfuric acid (about 5-30% SO$_3$) at temperatures ranging from about −15° C. to about 50° C.

In one illustrative approach, illustrated below, a precursor is formed, then allowed to react to form DAPO, which is in turn allowed to react to form LLM-105.

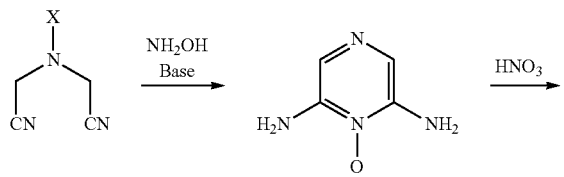

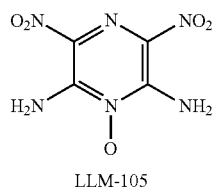

LLM-105

X = Cl, NO, NO$_2$, ...
Base: Na$_2$CO$_3$, NaHCO$_3$, amines, ...

2-amino-6-R-substituted-pyrazine synthesis

The synthesis of 2-amino-6-R-substituted-pyrazines follows a similar approach to that for the synthesis of DAPO. In general, N—X-bis(cyanomethyl)amine is reacted with one or more of: an alkylamine; an arylamine; an alkylalcohol; an arylalkylalcohol; an etheralcohol; and a tertiaryaminoalkylalcohol; and an aryl alcohol in the presence of a base, such as one or more of the bases listed herein. The product is a 2-amino-6-alkylaminopyrazine, a 2-amino-6-arylaminopyrazine, a 2-amino-6-alkoxypyrazine, a 2-amino-6-arylalkylaminopyrazine, a 2-amino-6-etheralkoxypyrazine, a 2-amino-6-tertiaryaminoalkylalkoxypyrazine or a 2-amino-6-aryloxypyrazine, respectively. Product yields of up to about 70% are achievable.

A general reaction using an amine is presented immediately below.

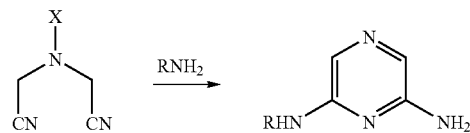

A general reaction using an alcohol is presented immediately below.

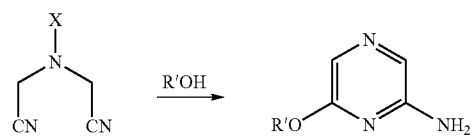

Suitable amines include, but are not limited to, any primary or secondary amines (preferably aliphatic amines) or alcohol amine, or substituted derivative of these. In some embodiments, the amines are aliphatic amines with alkyl or substituted alkyl lengths of $C_1$-$C_{20}$. Other examples include n-butylamine, ethanolamine, 3,3-dimethylaminopropylamine, 1,4-diaminobutane, cyclohexylamine, diethylamine and the amines shown immediately below.

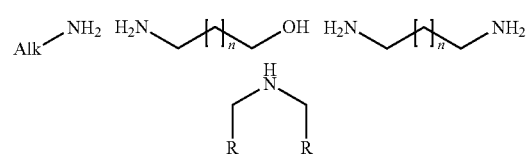

n = 0-12
R = C$_1$—C$_{20}$

Suitable aryl groups include, but are not limited to, phenyl, pyridyl, thiophenyl, napthyl, pyrazolyl, imidazolyl, 1,2,4-triazolyl, 1,2,3-triazolyl, tetrazolyl, pyrrolyl, and substituted derivatives thereof, an example of which is presented below.

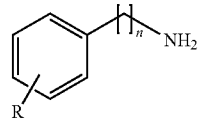

n = 0-12
R = —Cl, —I, —Br, —OR, —NR$_2$, alkyl, aryl, heterocycle, —CN, —COOR, CONR$_2$, It should be noted that, thus far, aryl amines such as aniline or 2-aminopyridine did not yield the desired 2-amino-6-arylaminopyrazine using the reaction conditions described herein.

Illustrative alcohols include ethanol; n-butanol; an aliphatic, arylalkyl or aryl alcohol such ethanol; n-butanol, phenethyl alcohol; etc.

Solvents that may be used in the conversion of the precursor to a substituted pyrazine include aliphatic alcohols ($C_1$-$C_6$), polar aprotic solvents such as dimethylformamide, dimethylsulfoxide, and N-methylpyrrolidinone, ethers, water, etc.

In one approach, N—X-bis(cyanomethyl)amine is reacted with an alkylamine in the presence of base. The product is a 2-amino-6-alkylaminopyrazine.

In another approach, N—X-bis(cyanomethyl)amine is reacted with an arylamine in the presence of base. The product is a 2-amino-6-arylaminopyrazine.

In yet another approach, N—X-bis(cyanomethyl)amine is reacted with an alkylalcohol in the presence of base. The product is a 2-amino-6-alkoxypyrazine.

In a further approach, N—X-bis(cyanomethyl)amine is reacted with an aryl alcohol in the presence of base. The product is a 2-amino-6-aryloxypyrazine.

In one example, addition of aliphatic amines in the presence of base to the precursor, N—X-substituted iminodiacetonitrile, yields 2-amino-6-(alkylamino)pyrazine.

In another example, addition of aryl-substituted an alkylamine in the presence of base to the precursor, N—X-substituted iminodiacetonitrile, yields 2-amino-6-(arylmethylamino)pyrazine.

In further examples, depicted immediately below, the precursor is formed, then reacted to form various materials.

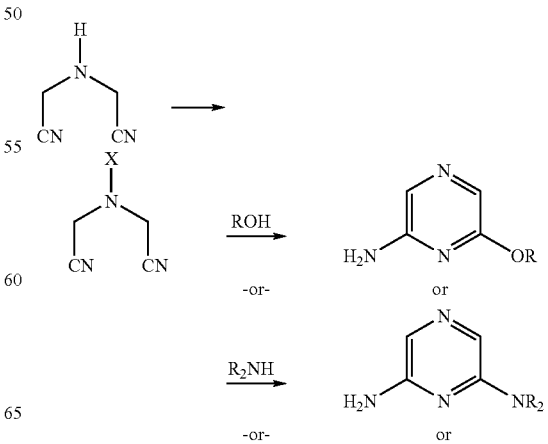

-continued

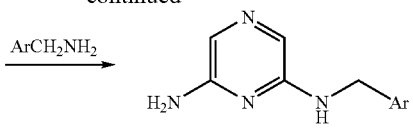

FIG. 1 depicts a general illustrative reaction 100 for preparing aminopyrazines from N-nitroso-bis(cyanomethyl)amine, with the amine-based reactants and corresponding aminopyrazine products listed in table format below the general reaction.

2,6-diaminopyrazine synthesis

Addition of ammonia to the precursor, N—X-substituted iminodiacetonitrile, yields 2,6-diaminopyrazine.

EXPERIMENTAL

1. Preparation of N-chloro-bis(cyanomethyl)amine

Iminodiacetonitrile (6.44 g, 67.7 mmol) was suspended in methanol (33 ml) at 0-5° C. (ice-water cooling bath), tert-Butylhypochloride (7.71 g, 71.1 mmol) was added by dropwise addition. The reaction temperature was controlled to remain below 10° C. When the addition was completed, the clear pale yellow solution was stirred on the cooling bath for 1.0 hr and then at room temperature for another 1.0 hr. The conversion of the reaction was 100% and it was the only product in the mixture. The product may be used without further purification.

2. Preparation of 2,6-diaminopyrazine-1-oxide from N-chloro-bis(cyanomethyl)amine To the solution of N-chloro-bis(cyanomethyl)amine (0.87 g, 6.75 mmol) in 8.0 ml of methanol was added hydroxylamine hydrochloride (0.47 g, 6.8 mmol) at 0-5° C. The reaction mixture was allowed to warm to room temperature within 20 hours. Triethylamine (2.8 ml, ~20.3 mmol) was added to the solution at 0-5° C. by stirring, and the addition speed was controlled so that the reaction temperature would not be over 15° C. After the addition was completed, the reaction mixture was stirred on the cooling bath for 10 minutes, then the cooling bath was removed, and the mixture was stirred at room temperature for 4 hours. The solvent was removed on a rotary evaporator and the residue was extracted with chloroform. The residue was recrystalized twice from water to give 0.12 g of DAPO, yield 14%. Nuclear magnetic resonance (NMR) spectroscopy showed that it was a pure product.

3. Preparation of 2,6-diaminopyrazine-1-oxide from N-chloro-bis(cyanomethyl)amine To the solution of N-chloro-bis(cyanomethyl)amine (0.87 g, 6.75 mmol) in 8.0 ml of methanol was added hydroxylamine hydrochloride (0.47 g, 6.8 mmol) at 0-5° C. The reaction mixture was allowed to warm to room temperature within 20 hours. The mixture was then added to the solution of $NaHCO_3$ (1.3 g, 15 mmol) in 10 ml of water at 70° C. After the addition was completed, the reaction mixture was refluxed for 30 minutes. The mixture was cooled down to 0-5° C. and the precipitate was collected by filtration. The solid was recrystalized again from water to give DAPO, 0.18 g (21%).

4. Preparation of 2,6-diaminopyrazine-1-oxide from N-nitroso-bis(cyanomethyl)amine N-Nitroso-bis(cyanomethyl)amine (5.0 g, 40.3 mmol) was suspended in 25 ml of methanol at 0-5° C. (ice-water). Hydroxylamine hydrochloride (2.90 g, 41.7 mmol) was added in 3 portions with stirring. To the mixture, triethylamine (11.0 ml, 79.0 mmol) was added by dropwise addition so that the temperature of the reaction would not exceed 15° C. After the addition was completed, all solids dissolved and the reaction mixture appeared as pale yellow clear solution. The mixture was stirred on the cooling bath for 20 minutes. The ice-water bath was replaced with a water bath (~20° C.) and the mixture was stirred on the bather for another 1.5 hr. The precipitate was collected by filtration, washed with methanol, and dried to give DAPO, 2.90 g. NMR showed that the compound was pure. The filtrate was treated by chloroform and the residue was recrystalized from water to give 0.39 g of DAPO. The total yield was 66%.

5. Preparation of 2,6-diaminopyrazine-1-oxide from N-nitroso-bis(cyanomethyl)amine Sodium bicarbonate (5.0 g, 59.5 mmol) in 40 ml of water was heated to 65° C. to give clear solution. The mixture of N-nitroso-bis(cyanomethyl)amine (3.0 g, 24.2 mmol) and hydroxylamine hydrochloride (1.76 g, 25.3 mmol) was added in portions (the gas was releasing from the reaction). After addition, the reaction mixture was heated at 70° C. for 15 minutes, 1.0 g of charcoal was added and the mixture was heated for an additional 5 minutes. The solids phases were removed by filtration and the filtrate was concentrated on a rotary evaporator to leave about 10 ml solution. After cooling the filtrate down to room temperature, the crystals were collected by filtration, and washed in water to give 0.201 g DAPO (yield 6%).

6. Preparation of 2,6-diaminopyrazine-1-oxide from N-nitro-bis(cyanomethyl)amine N-Nitro-bis(cyanomethyl)amine (0.80 g, 5.7 mmol) was suspended in 10 ml of methanol. Hydroxylamine hydrochloride was added in three portions at 0-5° C. Triethylamine (2.1 ml, 15.0 mmol) was added by dropwise addition, controlling the reaction temperature to remain below 10° C. After the addition was completed, the reaction mixture was stirred on the cooling bath for 20 minutes. The cooling bath was replaced with water bath (~20° C.) and the mixture was stirred at the temperature for another 3.0 hours. The solvent was removed on a rotary evaporator and the black residue was extracted using chloroform. The residue was recrystalized from water to give 50 mg DAPO (yield 7%).

7. 2,6-diamino-3,5-dinitropyrazine-1-oxide

Into a 3 Liter 3-necked round-bottomed flask equipped with a thermometer and drying tube was placed 30% fuming $H_2SO_4$ (105 ml) and conc. $H_2SO_4$ (200 ml) to make a 10% fuming sulfuric acid solution. Upon mixing an exotherm occurs and the temperature rises to about 40° C. With vigorous stirring, the reaction mixture is cooled to <10° C. and 2,6-diaminopyrazine-1-oxide (DAPO) (50 g, 0.4 mol) is added portion-wise at <10° C. The mixture is stirred vigorously until a solution is realized. The reaction mixture is cooled to 10° C. with ice bath cooling and 100% $HNO_3$ (60 mL, 90 g, 1.45 mol) is added dropwise at <15° C. The addition takes about 0.5 hours. The red-orange reaction mixture is stirred at 5-10° C. for 1 hour, allowed to warm to room temperature and stir 2 hours and poured into ice water (4 liter) to yield a voluminous yellow solid. The precipitate is collected by suction filtration, washed with water (1 liter) and MeOH to yield 54 g (64%) of essentially pure LLM-105 as a yellow powder.

An IR spectrum and $^1$H-nmr spectrum showed it to be essentially pure LLM-105.

The reaction products may be used in a wide variety of applications, and potentially any application in which the chemicals listed above are useful. For example, the products may be used in pharmaceutical applications, as reactants in other reactions, explosive applications, etc.

LLM-105 is an insensitive energetic compound for both conventional and nuclear weapon applications. Other illustrative uses of LLM-105 include, but are not limited to, deep oil well perforation, insensitive booster applications, insensitive munitions, etc.

While various embodiments have been described above, it should be understood that they have been presented by way of example only, and not limitation. Thus, the breadth and scope of a preferred embodiment should not be limited by any of the above-described exemplary embodiments, but should be defined only in accordance with the following claims and their equivalents.

What is claimed is:

1. A method for synthesizing a pyrazine-containing material, comprising the step of: contacting $XN(CH_2CN)_2$ with a base and a reagent selected from a group consisting of a primary amine, a secondary amine, an optionally substituted aliphatic amine, an arylalkylamine, a heteroarylalkylamine, an alcoholamine, an aryl alcoholamine, hydroxylamine, an acid addition salt of hydroxylamine and an alcohol, wherein X is a leaving group and wherein the base is selected from a group consisting of a metal hydroxide, a secondary amine, a tertiary amine and pyridine.

2. The method of claim 1, wherein the reagent is selected from a group consisting of a primary amine, a secondary amine, an optionally substituted aliphatic amine, an arylalkylamine, an alcoholamine, an aryl alcoholamine, hydroxylamine, an acid addition salt of hydroxylamine and an alcohol.

3. The method of claim 1, wherein $XN(CH_2CN)_2$ is contacted with a reagent selected from a group consisting of a primary amine, a secondary amine, an arylalkylamine, a heteroarylalkylamine and an alcoholamine.

4. The method of claim 1, wherein $XN(CH_2CN)_2$ is contacted with a reagent selected from a group consisting of hydroxylamine and an acid addition salt of hydroxylamine.

5. The method of claim 4, further comprising contacting with nitric acid in the presence of sulfuric acid.

6. The method of claim 1, wherein $XN(CH_2CN)_2$ is contacted with an optionally substituted aliphatic amine.

7. The method of claim 6, wherein the aliphatic of the optionally substituted aliphatic amine is optionally substituted $C_1$-$C_{20}$ alkyl.

8. The method of claim 1, wherein $XN(CH_2CN)_2$ is contacted with an arylalkylamine.

9. The method of claim 8, wherein the aryl of the arylalkylamine is selected from a group consisting of phenyl, pyridyl, thiophenyl, naphthyl, pyrazolyl, imidazolyl, triazolyl, tetrazolyl and pyrrolyl.

10. The method of claim 1, wherein X is selected from a group consisting of Cl, Br, I, NO, $NO_2$, OH, alkoxy and an ester.

11. The method of claim 1, further comprising forming $XN(CH_2CN)_2$ from $HN(CH_2CN)_2$.

12. A method for synthesizing 2-amino-6-(alkylamino)pyrazine, 2-amino-6-(arylalkylamino)pyrazine, 2-amino-6-(arylamino)pyrazine, 2-amino-6-alkoxypyrazine, 2-amino-6-(alkoxyalkoxy)pyrazine, 2-amino-6-(tertiaryaminoalkylalkoxy)pyrazine or 2-amino-6-aryloxypyrazine, comprising the step of: contacting $XN(CH_2CN)_2$ with a base and a reagent selected from a group consisting of an alkylamine, an arylalkylamine, an arylamine, an alkylalcohol, an arylalkylalcohol, an alkoxyalcohol, a tertiaryaminoalkylalcohol and an arylalcohol, wherein X is selected from a group consisting of Cl, Br, I, $NO_2$, OH, trifluoroacetate, mesylate, tosylate, alkoxy and an ester.

13. A method for synthesizing 2-amino-6-(aliphatic amino)pyrazine, comprising the step of: contacting $XN(CH_2CN)_2$ with a base and an optionally substituted aliphatic amine, where X is a leaving group.

14. The method of claim 13, wherein the aliphatic of the optionally substituted aliphatic amine is selected from a group consisting of an optionally substituted primary amine, an optionally substituted secondary amine and an optionally substituted alcoholamine.

15. The method of claim 13, wherein the aliphatic of the optionally substituted aliphatic amine is optionally substituted $C_1$-$C_{20}$ alkyl.

16. The method of claim 13, wherein the base is selected from a group consisting of a metal hydroxide, a metal alkoxide, a metal carbonate, a metal bicarbonate, a secondary amine, a tertiary amine and pyridine.

17. The method of claim 13, further comprising forming $XN(CH_2CN)_2$ from $HN(CH_2CN)_2$.

18. A method for synthesizing 2-amino-6-(arylalkylamino)pyrazine, comprising the step of: contacting $XN(CH_2CN)_2$ with a base and an arylalkylamine, where X is a leaving group.

19. The method of claim 18, wherein the aryl of the arylalkylamine is selected from a group consisting of phenyl, pyridyl, thiophenyl, naphthyl, pyrazolyl, imidazolyl, triazolyl, tetrazolyl and pyrrolyl.

20. The method of claim 18, wherein the base is selected from a group consisting of a metal hydroxide, a metal alkoxide, a metal carbonate, a metal bicarbonate, a secondary amine, a tertiary amine and pyridine.

21. The method of claim 18, further comprising forming $XN(CH_2CN)_2$ from $HN(CH_2CN)_2$.

22. A method for synthesizing 2,6-diaminopyrazine, comprising the step of: contacting $XN(CH_2CN)_2$ with ammonia, where X is a leaving group.

23. The method of claim 22, wherein X is selected from a group consisting of Cl, Br, I, NO, $NO_2$, alkoxy and an ester.

24. The method of claim 22, further comprising forming $XN(CH_2CN)_2$ from $HN(CH_2CN)_2$.

25. A method for synthesizing 2,6-diaminopyrazine-1-oxide, comprising the step of: contacting $XN(CH_2CN)_2$ with a base and a reagent selected from a group consisting of hydroxylamine and an acid addition salt of hydroxylamine, wherein X is selected from a group consisting of Cl, Br, I, $NO_2$, OH, alkoxy and an ester.

26. The method of claim 25, wherein the base is selected from a group consisting of a metal hydroxide, a metal alkoxide, a metal carbonate, a metal bicarbonate, a secondary amine, a tertiary amine and pyridine.

27. The method of claim 25, wherein 2,6-diaminopyrazine-1-oxide is produced in a yield between 60% and 80%.

28. The method of claim 25, further comprising forming $XN(CH_2CN)_2$ from $HN(CH_2CN)_2$.

29. A method for synthesizing 2,6-diamino-3,5-dinitropyrazine-1-oxide, comprising the steps of: (i) contacting $XN(CH_2CN)_2$ with a reagent selected from a group consisting of hydroxylamine and an acid addition salt of hydroxylamine, where X is a leaving group; and (ii) contacting 2,6-diaminopyrazine-1-oxide with nitric acid in the presence of sulfuric acid.

30. The method of claim 29, wherein X is selected from a group consisting of Cl, Br, I, NO, $NO_2$, OH, alkoxy and an ester.

31. The method of claim 29, wherein the contacting is performed at a temperature between −15° C. and 50° C.

32. The method of claim 29, wherein the contacting is performed at a temperature between −15° C. and 0° C.

33. The method of claim 29, wherein the contacting is performed at a temperature between 0° C. and 50° C.

\* \* \* \* \*